United States Patent

Rueter et al.

[11] Patent Number: 5,863,391
[45] Date of Patent: Jan. 26, 1999

[54] PURIFICATION OF A METHANOL STREAM

[75] Inventors: Michael A. Rueter, Norristown; John C. Jubin, Jr., West Chester, both of Pa.

[73] Assignee: ARCO Chemical Technology, L.P., Greenville, Del.

[21] Appl. No.: 911,972

[22] Filed: Aug. 15, 1997

[51] Int. Cl.$^6$ .............................. B01D 3/40; C07C 27/26
[52] U.S. Cl. .............................. 203/14; 203/18; 203/52; 203/55; 203/56; 203/64; 203/65; 203/78; 203/79; 203/DIG. 9; 203/DIG. 23; 568/913; 568/916
[58] Field of Search .............................. 203/DIG. 23, 64, 203/18, 51, 52, 53, 55, 78–80, 63, DIG. 9, 14, 3, 56; 568/913, 916, 492, 487

[56] References Cited

U.S. PATENT DOCUMENTS

| | | | |
|---|---|---|---|
| 3,881,996 | 5/1975 | Schmidt | 203/41 |
| 4,140,588 | 2/1979 | Schmidt | 203/92 |
| 4,388,154 | 6/1983 | Hochstein et al. | 203/DIG. 23 |
| 4,584,063 | 4/1986 | Berg et al. | 203/51 |
| 4,597,834 | 7/1986 | Beer et al. | 203/51 |
| 4,620,901 | 11/1986 | Berg et al. | 203/51 |
| 4,824,976 | 4/1989 | Clerici et al. | 549/531 |
| 4,833,260 | 5/1989 | Neri et al. | 549/531 |
| 4,971,661 | 11/1990 | Meyer et al. | 203/54 |
| 5,000,825 | 3/1991 | Shih et al. | 203/3 |
| 5,523,426 | 6/1996 | Jubin, Jr. et al. | 549/531 |
| 5,591,875 | 1/1997 | Chang et al. | 549/531 |
| 5,621,122 | 4/1997 | Saxton et al. | 549/529 |
| 5,646,931 | 7/1997 | Crocco et al. | 549/531 |

FOREIGN PATENT DOCUMENTS

| | | | |
|---|---|---|---|
| 0732327 | 9/1996 | European Pat. Off. . | |
| 0136453 | 7/1979 | Germany | 203/DIG. 23 |
| 0146453 | 2/1981 | Germany | 203/DIG. 23 |
| 8022849 | 8/1993 | Japan . | |
| 8001246 | 9/1993 | Japan . | |
| 5320086 | 2/1994 | Japan . | |
| 8787761 | 11/1981 | U.S.S.R. . | |
| 1313849 | 5/1987 | U.S.S.R. . | |

*Primary Examiner*—Virginia Manoharan
*Attorney, Agent, or Firm*—Stephen D. Harper

[57] ABSTRACT

Acetaldehyde may be effectively removed from a contaminated methanol stream using a distillation method wherein a solvent stream containing a relatively heavy polar compound such as water or propylene glycol is utilized as an extractive distillation solvent. Following the separation of the polar compound from the bottoms stream obtained by extractive distillation, the purified methanol may be recycled for use as a reaction solvent in an olefin epoxidation process.

17 Claims, 1 Drawing Sheet

PURIFICATION OF A METHANOL STREAM

FIELD OF THE INVENTION

This invention pertains to the purification of a methanol stream contaminated with acetaldehyde. In particular, the invention relates to an extractive distillation method wherein a polar substance such as water or propylene glycol is used to enhance the volatility of acetaldehyde relative to methanol, enabling the acetaldehyde impurities to be more easily separated as an overhead stream from the methanol.

BACKGROUND OF THE INVENTION

In recent years, the production of propylene oxide from propylene using hydrogen peroxide as an oxidant and a titanium-containing zeolite as a catalyst has been proposed. Methanol is a particularly preferred reaction solvent for such purposes, as it tends to promote high catalyst activity and selectivity. Epoxidation processes of this type are described, for example, in U.S. Pat. Nos. 5,591,875, 4,833,260, 5,621,122, 5,646,314, and 4,824,976, EP Pub. No. 0732327, and Clerici et al., *J. Catalysis* 129, 159–167 (1991), the teachings of which are incorporated herein by reference in their entirety. Although such processes are capable of providing exceptionally high selectivity to propylene oxide, minor quantities of certain by-products such as acetaldehyde are inevitably formed.

The methanol which is recovered following the separation of unreacted propylene and propylene oxide from the crude epoxidation reaction product often is contaminated with acetaldehyde. In addition to the acetaldehyde produced during epoxidation, acetaldehyde may be generated during the methanol recovery steps. Normally, it will be economically advantageous to recycle the recovered methanol for use in the epoxidation process. While low concentrations of acetaldehyde generally may be present in the epoxidation reaction mixture without deleterious effect on the epoxidation, in a continuous process the acetaldehyde will tend to accumulate in the methanol recycle stream to an unacceptable level. At high concentrations, for example, the accumulated acetaldehyde can contaminate the propylene oxide being produced. The complete separation of acetaldehyde from propylene oxide is difficult, however. It will thus be highly desirable to develop a means by which at least a portion of the acetaldehyde may be effectively separated from the recovered methanol prior to the methanol being reintroduced to the epoxidation reactor.

SUMMARY OF THE INVENTION

This invention provides a method of removing acetaldehyde from an impure methanol stream comprising (a) introducing the impure methanol stream into an intermediate section of an extractive distillation zone, (b) introducing an extractive solvent stream comprised of a polar substance selected from the group consisting of water, glycols, glycol ethers and mixtures thereof to an upper section of said extractive distillation zone, (c) distilling acetaldehyde overhead from said extractive distillation zone, and (d) recovering from a lower section of said extractive distillation zone a bottoms stream comprising methanol and the polar substance and having a reduced acetaldehyde concentration as compared to the impure methanol stream.

The bottoms stream may thereafter be introduced into an intermediate section of a fractional distillation zone, the methanol distilled overhead from said fractional distillation zone, and a second bottoms stream comprising the polar substance recovered from a lower section of said fractional distillation zone.

In another embodiment of the invention, only a portion of the impure methanol stream is fed to the extractive distillation zone with the remaining portion being fed directly to the fractional distillation zone in the same manner as the bottoms stream from the extractive distillation zone.

In yet another embodiment of the invention, the impure methanol stream is additionally comprised of at least one polar substance other than water, and the second bottoms stream is subjected to an additional fractional distillation to remove water overhead and to obtain a third bottoms stream comprised of the polar substance which is recycled for use as the extractive solvent stream in step (c).

DETAILED DESCRIPTION OF THE INVENTION

Figure 1:
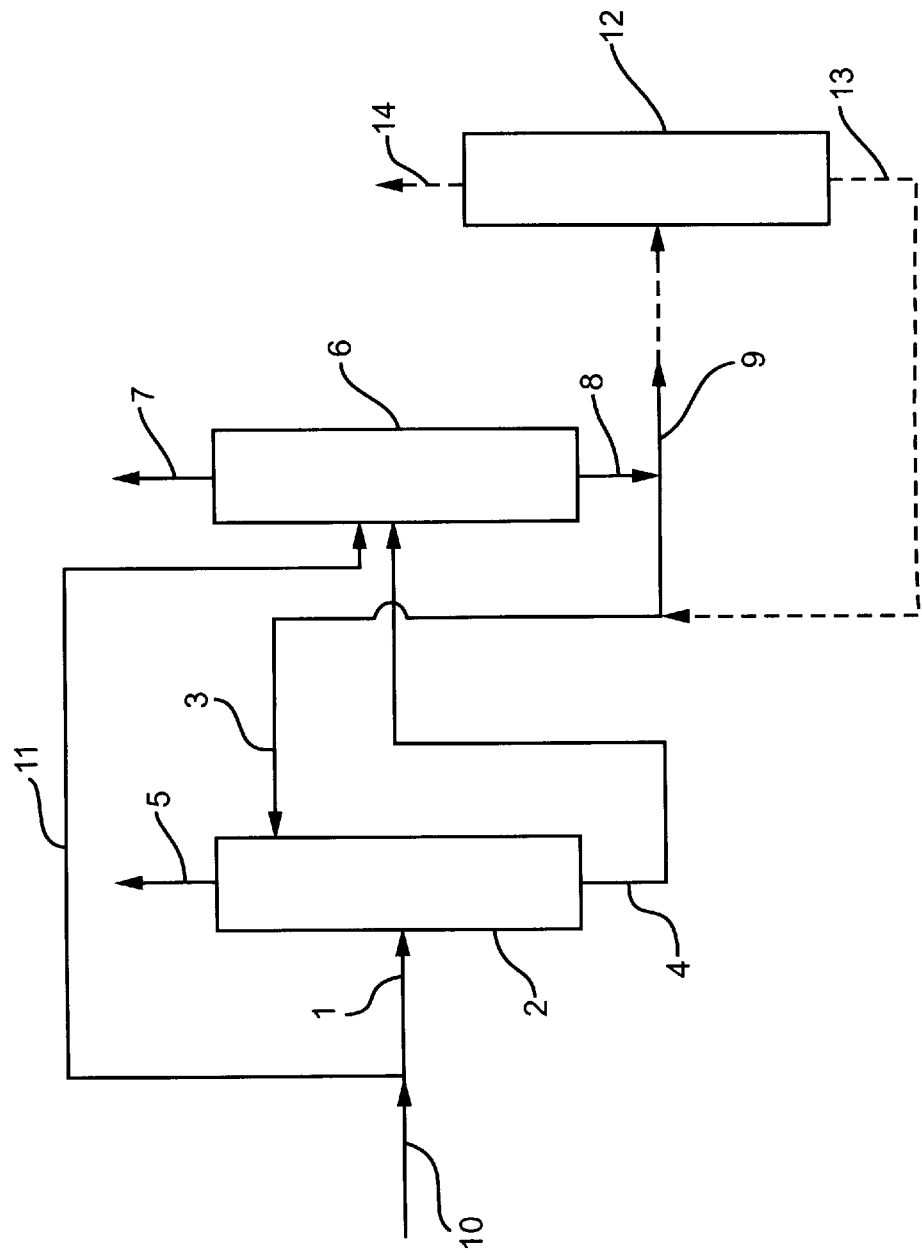
FIG. 1, to be explained in more detail hereafter, illustrates in schematic form an embodiment of the invention.

The impure methanol stream treated in accordance with the process of this invention is typically obtained by subjecting a crude epoxidation reaction product containing methanol as a solvent to an initial fractionation or series of fractionations wherein most or all of the unreacted propylene and the propylene oxide product are first removed by means of distillation or the like. The crude epoxidation reaction product may be generated by reacting propylene and hydrogen peroxide in a liquid phase comprised of methanol in the presence of a catalytically effective amount of a titanium-containing zeolite such as titanium silicalite (TS-1), as described in the references listed in the Background section of this application. Depending upon the epoxidation conditions and initial fractionation means employed, the impure methanol stream generally will have a composition comprised of the following components, in percent by weight:

| | |
|---|---|
| Methanol | 60 to 90 |
| Acetaldehyde | 0.01 to 0.1 |
| Water | 5 to 40 |
| Glycols, glycol ethers, other heavy impurities | 0.1 to 2 |

Other components may, of course, also be present such as propylene, propylene oxide and reaction by-products and other impurities; typically, however, methanol will comprise at least 60 weight percent of the impure methanol stream. Any water or other polar substance present in the feed is taken into consideration in the calculation of the amount of polar substance to be supplied to the extractive distillation. Whatever the content of polar substance in the feed, however, the amount of polar substance supplied in a separate extractive solvent stream is at least about 25% by weight, based on the weight of the impure methanol stream. The amount of polar substance introduced into the extractive distillation zone is preferably 40 to 60 weight percent of the impure methanol stream feed.

The extractive distillation is suitably carried out in any convenient distillation column or tower appropriate for the distillation of methanol. The column or tower is equipped with an appropriate reflux condensing means and an appropriate reboiler heating means. For best results, the extractive distillation zone should contain at least 10 theoretical plates and ordinarily will contain 20 to 30 theoretical plates. The maximum number of theoretical plates is limited only by economic considerations. A single distillation column or tower is usually preferred for economic reasons, but the use of multiple distillation columns to accomplish the same result is not excluded.

The extractive solvent stream supplied to the extractive distillation zone will be comprised predominantly (e.g., at least 90 percent by weight) of one or more polar substances having volatilities less than that of methanol. Suitable polar substances for purposes of this invention include, water, glycols, glycol ethers and mixtures thereof. The term "glycols" refers to dihydric alcohols such as, for example, ethylene glycol, 1,2-propylene glycol, 1,3-propane diol, 1,4-butanediol, neopentyl glycol, 2-methyl 1,3-propanediol, 1,3-butanediol, 2,3-butanediol and the like and oligomers thereof such as diethylene glycol, tripropylene glycol, and the like. The term "glycol ethers" refers to mono- and di-ethers of glycols, and glycol oligomers, with monoalkyl ethers generally being preferred (e.g., propylene glycol monomethyl ether). It is preferred that the polar substance or mixture of polar substances selected comprise at least 85 weight percent, more preferably at least 95 weight percent of the extractive solvent stream. The feed point for the extractive solvent stream should be between the impure methanol stream feed point and the point at which the overhead stream comprising acetaldehyde is withdrawn from the extractive distillation zone. This will help to prevent contamination of the overhead stream by the extractive solvent stream, if so desired. Preferably, the extractive solvent stream is introduced to the extractive distillation zone at a point not less than 1 theoretical plate below the overhead stream withdrawal point and not less than 5 theoretical plates above the point where the impure methanol stream is introduced. Some methanol may be withdrawn overhead together with acetaldehyde; while it will generally be desirable to minimize the amount of overhead methanol, one of the advantages of this invention is that such losses typically represent only a small fraction (e.g., 1% or less) of the total amount of methanol in the impure methanol stream.

The point at which the impure methanol stream is introduced is an intermediate section of the extractive distillation zone, preferably from about 20% to 50% of the distance, in terms of theoretical plates, from the bottom to the top of the extractive distillation zone.

A suitable reflux/impure methanol stream feed ratio is important in achieving optimum results and generally will be in the range of from 0.5:1 to 1:1. The pressure under which the extractive distillation is suitably around atmospheric pressure, e.g., from about 8 up to about 50 psia (as measured at the top of the extractive distillation zone). The bottoms (reboiler) temperature will, of course, vary with the pressure but will typically be within the range of 90° C. to 120° C.

The extractive distillation conditions are selected so as to provide, at a minimum, a bottoms stream having a reduced acetaldehyde level as compared to the initial impure methanol stream. While the process of this invention is capable of being operated to remove all or substantially all (i.e., 99+%) of the initially present acetaldehyde, the conditions may also be readily adjusted if so desired so as to achieve a lower degree of acetaldehyde removal (e.g., 50 to 75%).

Where the initial impure methanol stream contains water in addition to methanol and it is desired to use an extractive solvent stream containing a polar substance or mixture of polar substances which is less volatile than water (although some water may be present as a mixture with the other polar substances) and to remove at least a portion of the water from the system so as to maintain a certain concentration of water in the extractive solvent stream, the following embodiment of the invention may be practiced. The bottoms product withdrawn from the fractional distillation zone is fed to an intermediate section of a second fractional distillation zone and fractionally distilled under conditions effective to take the desired amount of water overhead and to yield a third bottoms stream comprised of the polar substance which is withdrawn from a bottom section of the second fractional distillation zone. This third bottoms stream may then be recycled for use as the extractive solvent stream.

Another desirable embodiment of the present process is to feed only a portion (e.g., 5 to 30 percent by weight) of the impure methanol stream to the extractive distillation zone. The remainder is bypassed directly to the first fractional distillation zone, preferably being introduced to an intermediate section in the same manner as the first bottoms stream. The second portion of the impure methanol stream and the first bottoms stream may be fed separately or, if so desired, first combined prior to introducing into the first fractional distillation zone. This accomplishes the desired removal of a portion of the acetaldehyde from the impure methanol stream, but significantly reduces the energy and equipment costs of the process due to ability to utilize a smaller capacity extractive distillation zone than would be needed to handle the entire impure methanol stream.

In the accompanying drawing (FIG. 1) there is illustrated diagrammatically a representative system for carrying out the extractive distillation process of this invention. Thus, referring to the drawing, the reference numeral 1 designates the line for feeding a portion of the impure methanol stream to be treated to an extractive distillation zone 2. Heat may be supplied to the column or tower comprising the extractive distillation zone by means of a reboiler. Water is supplied as the extractive distillation solvent through line 3 in the form of an aqueous stream. The aqueous stream may additionally contain water-soluble organic substances such as glycols, glycol ethers and the like. The bottoms stream comprising methanol and water, but with a reduced acetaldehyde concentration, is withdrawn through line 4. The acetaldehyde is removed in vapor form as an overhead stream via line 5 and thereafter condensed and recovered for chemical value, burned as fuel, or sent to waste disposal. The bottoms stream is fed into an intermediate section of fractionator 6, which may be a conventional fractional distillation column or tower of appropriate materials and capacity, and subjected to fractional distillation. The remaining portion of the impure methanol stream supplied to the purification section described herein via line 10 is also fed into an intermediate section of fractionator 6 by way of line 11. Methanol in purified form is taken overhead via line 7 and may be recycled for use as a reaction solvent in an olefin epoxidation process. A bottoms stream comprised of water, which will generally also contain compounds less volatile under the distillation conditions than methanol, is withdrawn from a lower section of fractionator 6 through line 8. A portion of this bottoms stream may be returned by means of line 3 for further use as the extractive distillation stream in the extractive distillation step of the process. The remaining portion of the bottoms stream is withdrawn through line 9 for disposal. The amount of the bottoms stream removed in this manner may advantageously be adjusted to compensate for the amount of water generated from hydrogen peroxide as a co-product in the olefin epoxidation process. In the alternative embodiment of the invention where a polar substance other than water is used as the extractive solvent and said polar substance is less volatile than water, the aforedescribed extractive distillation process may be modified as follows. The polar substance (e.g., propylene glycol) is supplied through line 3. The bottoms stream withdrawn from a lower section of fractionator 6 through line 8 will be comprised of both water and the polar substance. Rather than returning a portion of this bottoms stream by means of line 3 for further use as the extractive distillation stream, the bottoms stream is instead directed through line 9 to an intermediate section of fractionator 12 and subjected to fractional distillation. Water is removed overhead from fractionator 12 via line 14 and a bottoms stream comprised of the polar substance is recycled for use via lines 13 and 3 for use as the extractive solvent stream in extractive distillation zone 2. The amount of water removed overhead is sufficient to maintain a constant concentration of water in the extractive solvent stream.

EXAMPLE

This example demonstrates the purification of an impure methanol stream in accordance with the present invention. The impure methanol stream has the following composition:

| Component | Wt. % |
|---|---|
| Methanol | 80.5 |
| Water | 18.3 |
| Acetaldehyde | 0.044 |
| Propylene Glycol | 0.23 |
| Other Heavy Components | 0.926 |

Of 100 parts by weight of this methanol stream, 13.3 parts are fed to a first distillation column (where extractive distillation is performed) while 86.7 parts are bypassed to a second tower (where fractional distillation is performed).

The first distillation tower contains 25 theoretical stages, including the reboiler. The impure methanol stream (13.3 parts) is fed to the 18th stage from the top and 6.8 parts by weight of water containing low levels of various organic impurities are fed to the second stage from the top. An overhead stream containing acetaldehyde is withdrawn from the top stage and condensed in a total condenser. The bulk of the methanol and water is withdrawn from the bottom stage (reboiler) and fed forward to the second tower. The first tower is operated at a reflux ratio (reflux to impure methanol feed) of 0.8. The pressure in the column condenser is set at 38 psia and the column operated with a pressure drop of 0.4 psi per tray such that the bottom pressure is approximately 50 psia. This results in a bottoms (reboiler) temperature of 112° C. and a top (condenser) temperature of 91° C.

Under these conditions, 75% of the acetaldehyde in the impure methanol stream fed to the first tower is recovered in the overhead distillate product. This represents 10% of the acetaldehyde in the total impure methanol stream. Of the amounts in the first tower feed, only 0.16% of the methanol and 0.23% of the water are taken overhead with the acetaldehyde. The compositions of the two streams obtained from the first tower are as follows:

| Component | Distillate (wt. %) | Bottoms (wt. %) |
|---|---|---|
| Methanol | 58.3 | 53.5 |
| Water | 18.2 | 42.8 |
| Acetaldehyde | 14.6 | 0.0073 |
| Propylene Glycol | 0 | 0.73 |
| Other Heavy Components | 0 | 2.96 |

The bottoms stream from the first tower (20 parts by weight) is fed to the second distillation tower together with the 86.7 parts of the initial impure methanol stream which bypasses the first tower.

The second distillation tower contains 20 theoretical stages (including reboiler). The feed streams are introduced at the 4th stage from the top. An overhead stream of purified methanol (86.8 parts) is withdrawn from the top stage and condensed in a total condenser. The balance of the water and heavy components is withdrawn from the bottom stage (reboiler). Of this bottoms stream, 13.3 parts are fed to the first distillation tower for reuse as the extractive solvent stream and the remainder is removed for disposal as waste.

The second tower operates at a reflux ratio (reflux to feed) of 0.44. The pressure in the column condenser is 160 psia and the column operated with a pressure drop of 0.5 psi per tray such that the bottom pressure is 170 psia. This results in a bottoms (reboiler) temperature of 187° C. and a top (condenser) temperature of 144° C.

Under the above-described conditions, 99.9% of the methanol in the feed to the second tower is recovered in the overhead distillate stream. The compositions of the two streams withdrawn from the second tower are as follows:

| Component | Distillate (wt. %) | Bottoms (wt. %) |
|---|---|---|
| Methanol | 92.6 | 0.48 |
| Water | 7.25 | 91.0 |
| Acetaldehyde | 0.0046 | 0 |
| Propylene Glycol | 0 | 1.72 |
| Other Heavy Components | 0 | 6.8 |

The distillate (overhead) stream may be recycled for use as a source of methanol in a propylene epoxidation process of the type described in EP Pub. No. 0732327 (corresponding to U.S. Ser. No. 08/404,657, now U.S. Pat. No. 5,693,834, filed Mar. 15, 1995).

We claim:

1. A method of removing acetaldehyde from an impure methanol stream comprising (a) introducing a first portion of the impure methanol stream into an intermediate section of an extractive distillation zone;

(b) introducing an extractive solvent stream comprised of a polar substance selected from the group consisting of water, glycols, glycol ethers and mixtures thereof into an upper section of said extractive distillation zone;

(c) distilling acetaldehyde overhead from said extractive distillation zone;

(d) recovering from a lower section of said extractive distillation zone a first bottoms stream comprising methanol and the polar substance and having a reduced acetaldehyde concentration as compared to the impure methanol stream;

(e) introducing the first bottoms stream and a second portion of the impure methanol stream into an intermediate section of a fractional distillation zone;

(f) distilling a purified methanol stream overhead from said fractional distillation zone; and (g) recovering from a lower section of the fractional distillation zone a second bottoms stream comprised of the polar substance and having a reduced methanol concentration as compared to the first bottoms stream.

2. The method of claim 1 wherein the amount of the extractive solvent stream introduced into said extractive distillation zone is at least 25 weight percent of the first portion of the impure methanol stream.

3. The method of claim 1 wherein the first portion of the impure methanol stream is from 5 to 30 percent by weight of the impure methanol stream.

4. The method of claim 1 wherein at least 60 weight percent of the impure methanol stream is comprised of methanol.

5. The method of claim 1 wherein the glycol is propylene glycol.

6. The method of claim 1 wherein at least 50% of the acetaldehyde in the first portion of the impure methanol stream is distilled overhead in step (c).

7. The method of claim 1 wherein the impure methanol stream is additionally comprised of water, the extractive solvent stream is comprised of at least one polar substance selected from the group consisting of glycols, glycol ethers, and mixtures thereof, and the second bottoms stream is subjected to an additional fractional distillation to remove water overhead and to obtain a third bottoms stream comprised of the polar substance which is recycled for use as the extractive solvent stream in step (b).

8. The method of claim 1 wherein the polar substance or mixture of polar substances comprises at least 85 weight percent of the extractive solvent stream.

9. A method of removing acetaldehyde from an impure methanol stream comprised of methanol, acetaldehyde, and water, said method comprising (a) introducing the impure methanol stream into an intermediate section of an extractive distillation zone;

(b) introducing an extractive solvent stream comprised of a polar substance less volatile than water and selected from the group consisting of glycols, glycol ethers and mixtures thereof into an upper section of said extractive distillation zone;

(c) distilling at least 50% of the acetaldehyde initially present in the impure methanol steam overhead from said extractive distillation zone;

(d) recovering from a lower section of said extractive distillation zone a first bottoms stream compromising methanol, water and the polar substance and having a reduced acetaldehyde concentration as compared to the impure methanol stream;

(e) introducing the first bottom streams into an intermediate section of a fractional distillation zone;

(f) distilling methanol overhead from said fractional distillation zone;

(g) recovering a second bottoms stream comprising the polar substance and water from a lower section of said fractional distillation zone; and (h) subjecting the second bottoms stream to an additional fractional distillation to remove water overhead and to obtain a third bottoms stream comprised of the polar substance which is recycled for use as the extractive solvent stream in step (b), wherein water is removed overhead in an an amount sufficient to maintain a constant concentration of water in the extractive solvent stream.

10. The method of claim 9 wherein the amount of the extractive solvent stream introduced into said extractive distillation zone is at least 25 weight percent of the impure methanol stream.

11. The method of claim 9 wherein the glycol is propylene glycol.

12. The method of claim 9 wherein the impure methanol stream is recovered from an epoxidation process wherein propylene is reacted with hydrogen peroxide using a titanium-containing zeolite as catalyst and methanol as a solvent.

13. The method of claim 9 wherein the impure methanol stream is comprised of 60–80 weight percent methanol, 0.01–0.1 weight percent acetaldehyde, and 5–40 weight percent water.

14. The method of claim 9 wherein the amount of the extractive solvent stream is from 40–60 weight percent of the impure methanol stream.

15. The method of claim 9 wherein a reflux/impure methanol stream feed ratio in the range of from 0.5:1 to 1:1 is maintained in said extractive distillation zone.

16. The method of claim 9 wherein the impure methanol stream is introduced to the extractive distillation zone at a point which is from 20% to 50% of the distance from the bottom to the top of said extractive distillation zone.

17. The method of claim 9 wherein the extractive distillation zone contains from 20 to 30 theoretical plates.

* * * * *